United States Patent [19]

Hametta

[11] Patent Number: 4,678,992
[45] Date of Patent: Jul. 7, 1987

[54] ELECTRONIC METAL DETECTOR

[75] Inventor: Allen W. Hametta, Arlington Heights, Ill.

[73] Assignee: Hi-Tech Systems, Corp., Carol Stream, Ill.

[21] Appl. No.: 513,103

[22] Filed: Jul. 12, 1983

[51] Int. Cl.$^4$ .................... G01B 7/14; G08B 21/00; G01F 15/06
[52] U.S. Cl. ................................ 324/208; 340/606; 324/173; 73/861.78
[58] Field of Search .............. 324/173, 174, 207, 208, 324/234, 236; 340/938, 870.39, 606–610; 73/861.77, 861.78

[56] References Cited

U.S. PATENT DOCUMENTS

| 3,451,041 | 6/1969 | Marosi et al. | 340/939 |
| 3,455,162 | 7/1969 | Michner et al. | 324/173 |
| 3,521,159 | 7/1970 | Morrow | 324/236 |
| 3,685,013 | 8/1972 | Brickner | 340/938 |

Primary Examiner—Ernest F. Karlsen
Assistant Examiner—Walter E. Snow
Attorney, Agent, or Firm—Michael J. Femal

[57] ABSTRACT

A metal detector circuit comprising an oscillator capable of sensing any type of metal in motion over a predetermined frequency. The oscillator supply voltage is derived from a feedback correction circuit which compensates for stationary metal as well as metal moving in a lower frequency past the sensing coil of the oscillator by adjusting the supply voltage of the oscillator to make up for Q losses. The higher frequencies are blocked by a DC time constant (low pass filter) and the sensor coil is able to see through stationary metal and detect a moving metal target on the other side thereof. The amplitude of the modulated signal from the oscillator remains nearly constant throughout its detection range by this supply voltage feedback correction circuit. The detection circuit also provides a reliable output signal indicating when the sensor portion is damaged due to an open or shorted coil circuit.

12 Claims, 3 Drawing Figures

ELECTRONIC METAL DETECTOR

BACKGROUND OF THE INVENTION

This invention relates, generally, to an industrial metal detector having a resonant circuit oscillator and more particular to a proximity detector for sensing any type of metal in motion past its sensing coil while the oscillator maintains a constant present level of oscillation throughout its sensing range.

Prior art proximity detectors using sensor coils are applied to a number of different industrial applications and one group of applications includes the measurement of speeds, flow rates or synchronization of motors or drives. In the synchronization mode, a circular device such as a wheel with protruding teeth thereon rotates past the sensor coil of the detector and produces a sync pulse. In motor speed detection, the detector senses the rotating teeth on the gear. Yet in another detection mode, a flow meter having an impeller with metallic vanes has liquid passing therethrough driving the impellor and rotating the ends of the vanes past the sensor coil producing the sync pulses. For these type of applications, passive and active magnetic sensors are often employed to convert the mechanical motion of ferrous gears and the like into electrical signals. These electrical signals are then translated into the position, revolution per minute and flow rate of the equipment being monitored.

Known passive and active metal detectors are often limited to sensing only the motion of ferrous metals passing across the path of their sensor coils. If such a metal detector incorporated a magnetic sensor then in a flow meter application, there exists the possibility of magnetic drag when it detects the movement of a ferrous impellor. This magnetic drag may cause the impellor to stop its rotary motion at slow flow rates and is further known to create wobbling of the impellor at high flow rates. This will obviously result in inaccurate measurements of the flow rate.

Moreover, prior art metal detectors, especially magnetic ones, are especially susceptible to misalignment in the field by the user due to the critical distance in which the sensor coil must be placed from its ferrous target. In addition, the output signal from a number of magnetic and other metal detectors is subject to run out as the distance between the sensor coil and its ferrous target increases or the target rotates with a wobble. These above critical factors in placement of the sensor coil in relation to its target as well as the dimensional variations in the target itself all contribute to unintelligible signals and inaccurate readings.

An object of the present invention is to provide an improved electronic metal detector which can detect all types of metal both ferrous and non-ferrous which move across its sensor coil.

Another object is to provide an improved electronic metal detector without magnetic drag to influence the accuracy of readings in a flow meter application.

Yet another object is to provide an improved electronic metal detector in which the placement of the sensor coil and the dimensional characteristics of its target are less critical in achieving accurate readings than in previous proximity detectors whether or not of the magnetic sensor type.

A further object is to provide an improved electronic metal detector which corrects for the presence of other metals in its sensing path that are stationary or moving at a slower predetermined rate while still detecting the desired metal target's movement.

A still further object is to provide an improved electronic metal detector capable of using generally any type of oscillator configuration and sensor coil yet sense metal targets over a greater distance from the sensor coil even though stationary metal is between the target and the sensor coil.

Another further object is to provide an improved electronic metal detector which gives a reliable indication that the sensor coil has been damaged by either a shortened or open coil circuit.

Further objects and advantages will become apparent form the following description wherein reference is made to the drawings.

SUMMARY OF THE INVENTION

An electronic metal detector in accordance with this invention comprises an oscillator circuit that seeks a preset level of oscillation amplitude by means of a DC time constant that is predetermined. The voltage generated by the oscillator is amplified and returned to the oscillator as a control voltage to maintain the original preset level of oscillation. This control voltage is actually the supply voltage for the oscillator circuit and without it the oscillator circuit would cease to oscillate. Therefore, this oscillator circuit is not a free running oscillator like previous detectors well known in the art.

Stationary metal placed in front of the sensor coil of the oscillator is electronically corrected for by means of the DC time constant portion of a feedback loop that provides the supply voltage to the oscillator. Therefore, the detector does not sense stationary metal in its path of detection but will see through that metal and sense a moving metal target on the other side thereof. A moving metal target, such as the vanes on an impeller in a flow meter housing, pass by the sensor coil with continuous rotary motion causing the oscillation amplitude to be modulated in relationship to each vane in the impellor. The modulated signal is decoded and the speed of the impellor is known and translated into a fluid flow through the meter. The DC time constant blocks the intelligence portion of the signal from being fed back to the oscillator for correction and thus the movement of the vanes is not corrected for but sensed.

The modulated oscillation is demodulated and amplified into DC pulses proportional to the modulation envelope. The minimum motion frequency is limited by the DC time constant which acts like a low pass filter, while the maximum motion frequency is limited by the response of the amplifier or oscillatory frequency.

Unlike the magnetic sensors, the non-magnetic detector of the present invention can detect non-magnetic metals or even non-ferrous metals like copper, aluminum, magnetic and non-magnetic stainless steel, foil, or brass. The detector can also detect metal in motion if the stationary metal is removed or moving at a much slower rate so that the correction circuit blocks it out. Since the detector can sense non-magnetic metals like stainless steel, a stainless steel impellor in a flow meter may be used, allowing the use of liquids with acidity previously unheard of in flow meter applications.

Still further advantages will become apparent from the following detailed description wherein reference is made to the drawings.

DETAILED DESCRIPTION OF THE INVENTION

Figure 1:
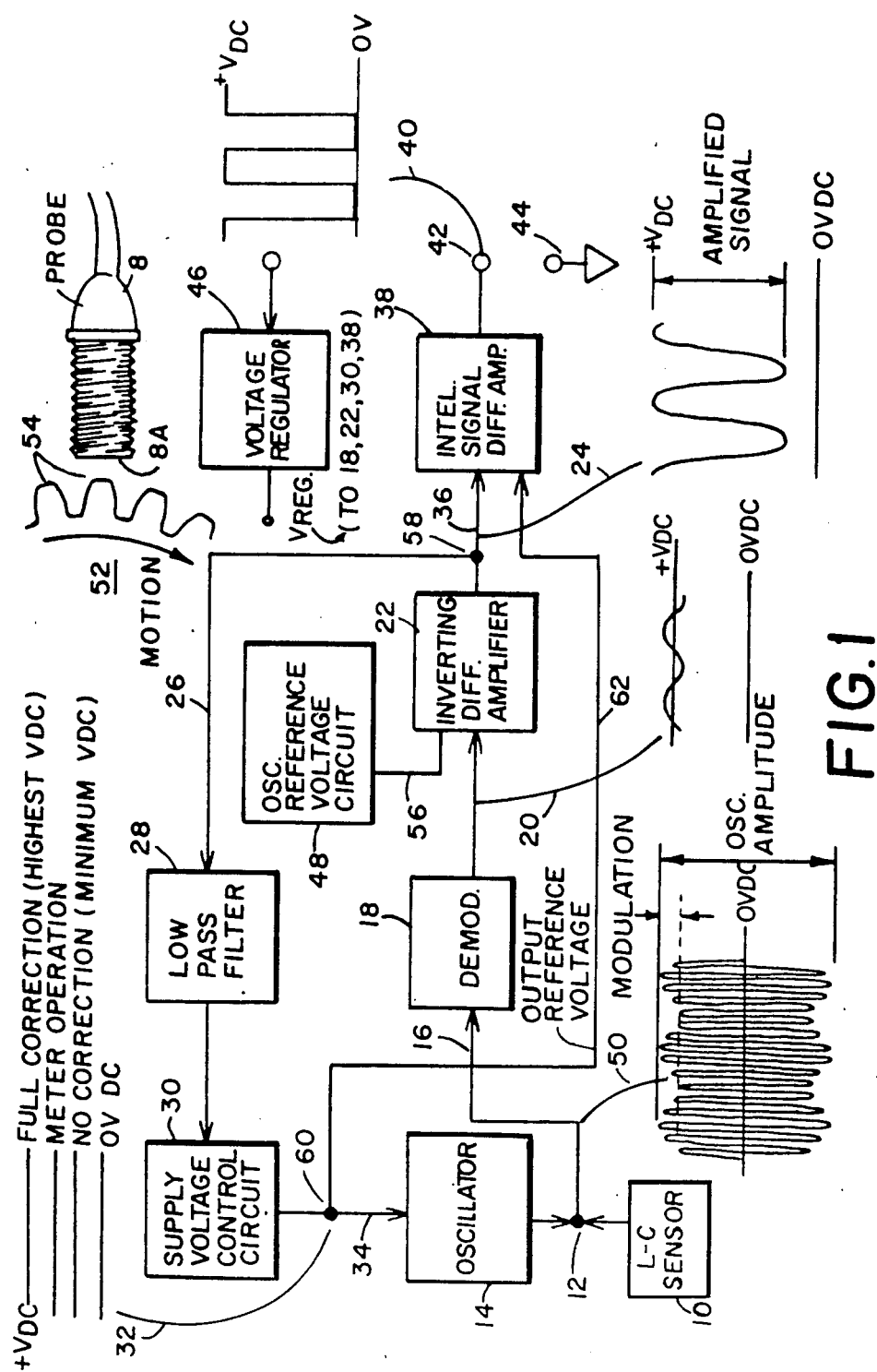
FIG. 1 is a block diagram of the detector made in accordance with the present invention.

Referring to FIG. 1, an electronic metal detector contained within a probe 8 comprises a sensor 10 located at one end 8A thereof which is connected to a first junction 12. Junction 11 is connected to the output of an oscillator circuit 14 generating a radio frequency (hereinafter called RF) signal. Sensor 10 modulates that RF signal when it senses the motion of metal thereacross. The junction 12 is connected to the input line 16 of a demodulator circuit 18. A DC signal 20 is an output of the demodulator and it serves as an input to an inverting amplifier 22 which generates an output signal 24 along dual output signal paths. One output signal path 26 feeds the conditioned signal 24 to a low pass filter circuit 28. The output of the low pass filter 28 provides an input signal to a supply voltage control circuit 30. The circuit 30 provides a feedback control voltage 32 and acts as the supply voltage for the oscillator circuit 14 via connecting line 34. Another output signal path 36 from the amplifier 22 is connected to an intelligence signal differential amplifier 38. This amplifier 38 provides an output signal 40 to the outside world via output terminal 42 and a ground terminal 44. A voltage regulator 46 supplies operating voltages to the circuits 18, 22, 30, 38 and a oscillator reference voltage circuit 48.

When a metal either ferrous or non-ferrous approaches in close proximity to the coil of sensor 10, the resultant Quality Factor (hereinafter called Q) of the resonant circuit drops yielding a lower RF voltage across the sensor 10 providing no feedback correction is made to the oscillator's supply voltage 32. If no metals are in the sensing range of sensor 10, then the Q of the resonant circuit is at its highest value and the RF voltage across the resonant circuit will be correspondingly at its highest.

Now when any metal is moved into the sensing field of the coil in the sensor 10 and the metal is essentially stationary, the RF voltage amplitude at the output junction 12 of oscillator 14 at first drops. This lower RF voltage produces a lower DC voltage 20 from the demodulator 18. The inverting differential amplifier 22 receives this lower DC voltage 20 and generates the higher output voltage 24. This higher DC voltage level 24 is passed through the low pass filter 28 which increases the output of the supply voltage control circuit 30.

Therefore, oscillator 14 is provided with a higher DC supply voltage 32 which returns the RF amplitude across the sensor 10 to its original set value. Now, when the sensor 10 detects moving metal in its path, a modulated RF signal 50 will be generated without the slow moving or stationary metal causing a degradation of its value. Because of this aforementioned feedback loop, the oscillator 14 is provided with a higher supply voltage 32 as the metal object slowly approaches the sensor 10. The RF voltage amplitude of the oscillator 14 instead of decreasing in value will remain generally constant as the oscillator 14 is driven harder due to the increase in its supply voltage 32. This generally constant RF output of oscillator 14 is the result of this unique supply voltage control feedback network which is unlike all other previous metal detectors in operation.

The feedback correction is not instantaneous but is delayed by the low pass filter 28 whose time constant is determined by the values of its RC circuit network. Continuous correction, as metal moves into the sensor field closer or farther away from the sensor 10, will occur as long as the speed of motion of the metal is slower than the time delay caused by the low pass filter 28. Conversely, if the speed of motion of the metal such as a gear 52 with teeth projections 54 rotating past the coil of the probe 8, is greater than this time delay then only partial, if any, feedback correction results.

The RF signal of oscillator 14 whether feedback corrected or not, is set by the oscillator reference voltage circuit 48. Circuit 48 generates a predetermined DC reference voltage to a non-inverting input 56 of the amplifier 22. The output signal of the amplifier 22 at a second junction point 58 is proportional to the difference between the output signal of the oscillator reference voltage circuit 48 and the output signal of the demodulator 18. This inverting differential amplifier 22 generates the DC output signal 24 which is fed back to the supply voltage control circuit 30 through the low pass filter 28. This DC voltage in turn provides the oscillator 14 with its necessary supply voltage needed to maintain the RF amplitude at a desired level as well as make the oscillator run itself. Without this voltage the oscillator would not work since there is no other supply voltage to the circuit.

Thus, if the oscillator reference voltage is increased, the RF amplitude across the sensor will correspondingly increase. Conversely, if the reference voltage is decreased the RF amplitude will correspondingly decrease.

Now when a metallic target moves toward and away from the sensor 10 of probe 8 at a repetitive rate greater than the upper limit of the low pass filter 28, the RF voltage at the output of the oscillator 14 is modulated with a signal from the sensor 10 that represents the back and forth motion of this metallic target such as the gear teeth 54. This modulated RF signal 50 from the sensor 10 is fed to the demodulator 18. The output signal of the demodulator 18 is a DC voltage with an AC signal component. The composite signal is fed to the inverting differential amplifier 22. The output signal 24 of amplifier 22 is also a DC voltage with an AC component. The DC voltage passes through the low pass filter 28 and maintains the average RF voltage across the sensor 10 constant. The AC component is blocked by the low pass filter. Thus, the AC component is not corrected in the feedback loop and will continue to appear at junction 58 or the output of amplifier 22.

The inputs of intelligence differential amplifier 38 are connected to two points within the detector circuit. One point is a third junction 60 which is connected to the output of the supply voltage circuit 30. Therefore, junction 60 provides the same DC voltage 32 as a reference voltage to a non-inverting input line 62 of amplifier 38 that is also provided to the oscillator 14 throughout the entire detector circuit operating range. The second point is the line 36 connected to the inverted input of amplifier 38 which is connected to the junction 58. The DC reference voltage establishes a threshold level at which the difference in signal levels between the first and second points of input to amplifier 38. If the signal level 24 form amplifier 22 is above the reference voltage on line 62 then the output of amplifier 38 results in a negative going output signal at terminals 42.

In the case where the metal movement is less than the time constant of the low pass filter 28, the output of amplifier 38 is constant high level DC voltage. This is because the two inputs to amplifier 38 are essentially the same value. In the case where the metal movement produces a repetitive AC signal whose frequency is above the upper limit of the low pass filter 28, the output of amplifier 38 is AC signal having the same frequency as the oscillatory movement of the metal with respect to sensor 10.

Now when a large metal object having protrusions and depressions such as the gear 52 or an impellor in a flow meter is moved in a substantially stationary position and the protrusions and depressions are moved in front of the sensor 10 at a repetitive rate, the action of the the metal detector circuit is a combination of the above described action. First the large metal object, when moved in front of sensor 10 in the probe 8 causes a supply voltage feedback correction which make up for the Q losses caused by the metal object. Second, if the repetitive rate of the motion is above the upper limit of low pass filter 28, the metal detector will give an output signal whose varying rate is the same as the motion of the metal object.

Now when this metal object has a second type of movement such as run-out or wobble (impellor or gear rotates past the sensor 10 in a less than perfect circular arc) whose rate of motion is less than the upper limit of the low pass filter, then the metal detector circuit adds a third action.

In short, there are the following three components to the output signal generated by the sensor during its detection of metal objects in motion: (1) is the steady Q loss caused by the large metal object; (2) is the high frequency repetitive change in Q caused by the protrusions and depressions on a gear for example; and (3) is the low frequency repetitive loss in Q caused by the second wobbling motion of the gear itself as a large metal object.

The first two components are handled the same as above. The third component causes the Q of sensor 10 to also change in relationship to the second repetitive motion of the metal. This component also modulates the RF signal at the sensor 10 and is fed to the demodulator 18 as previously stated. Since the output signal 20 of the demodulator 18 is a DC voltage with a composite AC signal component, this composite signal is passed on through the detection circuit. The composite signal is next fed to the inverting differential amplifier 22 which provides an output signal 24 of a DC voltage with the same AC component. The DC voltage and the low frequency AC component pass through the low pass filter 28 and returns the DC voltage across the sensor 10 to an essentially constant level except for the high frequency signal component. Once the initial delay of the low pass filter 28 has occurred, the low frequency changes in the feedback loop are more or less instantaneous. The high frequency component of the signal is blocked by the low pass filter 28 and the high and low frequency components both appear at the inverted input of the amplifier 38. The reference voltage 32 at the non-inverting input which is fed from the supply circuit 30 has both the DC and low frequency AC component.

Thus, the difference in signal levels of the two inputs to amplifier 38 is the high frequency component plus the DC component. In other words, the low frequency component is reduced to zero by the two inputs to amplifier 38. This design feature of the detector virtually eliminates this second low frequency component of the input signal from the sensor. This is also a major difference between the detector of the present invention versus all prior art devices.

Figure 3:
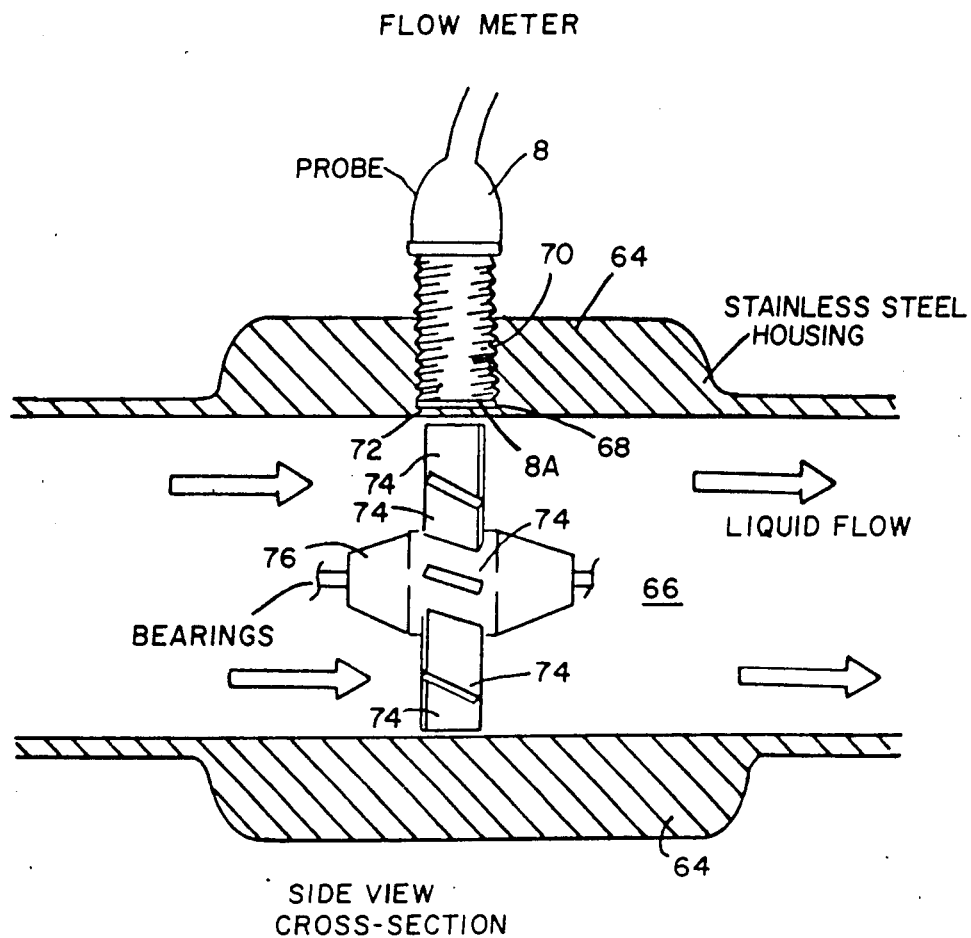
FIG. 3 is a flow meter application showing a side view cross section of the flow meter with the metal detector of FIG. 1 in a probe mounted in the flow meter housing.

For example, FIG. 3 shows a flow meter application where the sensor 10 in the probe 8 is screwed into a housing 64 of a metallic flow meter 66 which is usually made of non-magnetic stainless steel, the sensor 10 will come into contact with the blind hole bottom 68 of the housing 64. The bottom 68 of a probe hole 70 in the stainless steel housing 64 will change the parameters of the tuned resonant circuit of the sensor 10. The main parameter change in this case will be a decrease in the Q of the tuned circuit. However, because a stainless steel wall 72 next to the end 8A of the probe 8 is stationary, the feedback loop corrects for this Q change. Now the tuned circuit and sensor 10 will respond only to the motion of a metallic vane 74 on an impellor 76 that rotates past the bottom wall 72 of the mounting hole 70 in the housing 64 opposite the sensor 10. As long as this impellor 76 is in motion, the metal vanes 74 which pass near to and again away from the sensor 10 in a repetitive manner at a varying rate depending on the liquid flow through the meter 66, will create an intelligence signal output provided the upper frequency limit of the low pass filter is lower than the repetitive signal produced from the rotating vanes 74. The supply circuit 30 does not see this repetitive signal representing the intelligence signal as such but instead provides a nearly constant supply voltage to the oscillator 14. Thus, the output of the oscillator 14 is permitted to have an uncorrected modulation signal created by the impellor 76 passing its vanes 74 past the sensor 10. This intelligence signal is passed through amplifier 22 to amplifier 38 where it is further amplified for producing a usable output signal 40 at terminal 42.

As the sensor coil 10 is slowly unscrewed from the flow meter housing 64 while the detector is operating, the low pass filter 28 passes the slow motion signal to the circuit 30. The oscillator 14 will not see this slow movement as an additional input signal but will maintain a constant voltage across the sensor 10. Notwithstanding the action of the filter 28, the amplifier 22 which sees the modulated signal or the movement of the vanes 74 pass the sensor 10 and passes this intelligence signal to the amplifier 38 for amplification.

Although the Q of the tuned circuit is increasing in value as the sensor is unscrewed from the flow meter housing, the feedback loop continuously compensates for the higher oscillator output levels with a resultant lower voltage supplied to the oscillator 14. At some distance from the bottom of the mounting hole in the flow meter, the signal from the amplifier 22 falls below the threshold of amplifier 38 and the signal at output 42 ceases. This distance however is substantially greater than any known metal detectors. Even though the modulation level is at a very low amplitude that further amplification is not normally possible at this point due to the signal to noise ratio of the signals. However, in the detector circuit of the present invention, the intelligence signal can be obtained once again by simply increasing the gain of the amplifier. This enables the detector to see the intelligence signal as the sensor 10 is still further slowly removed from its mounting in the housing 64 of the flow meter.

Figure 2:
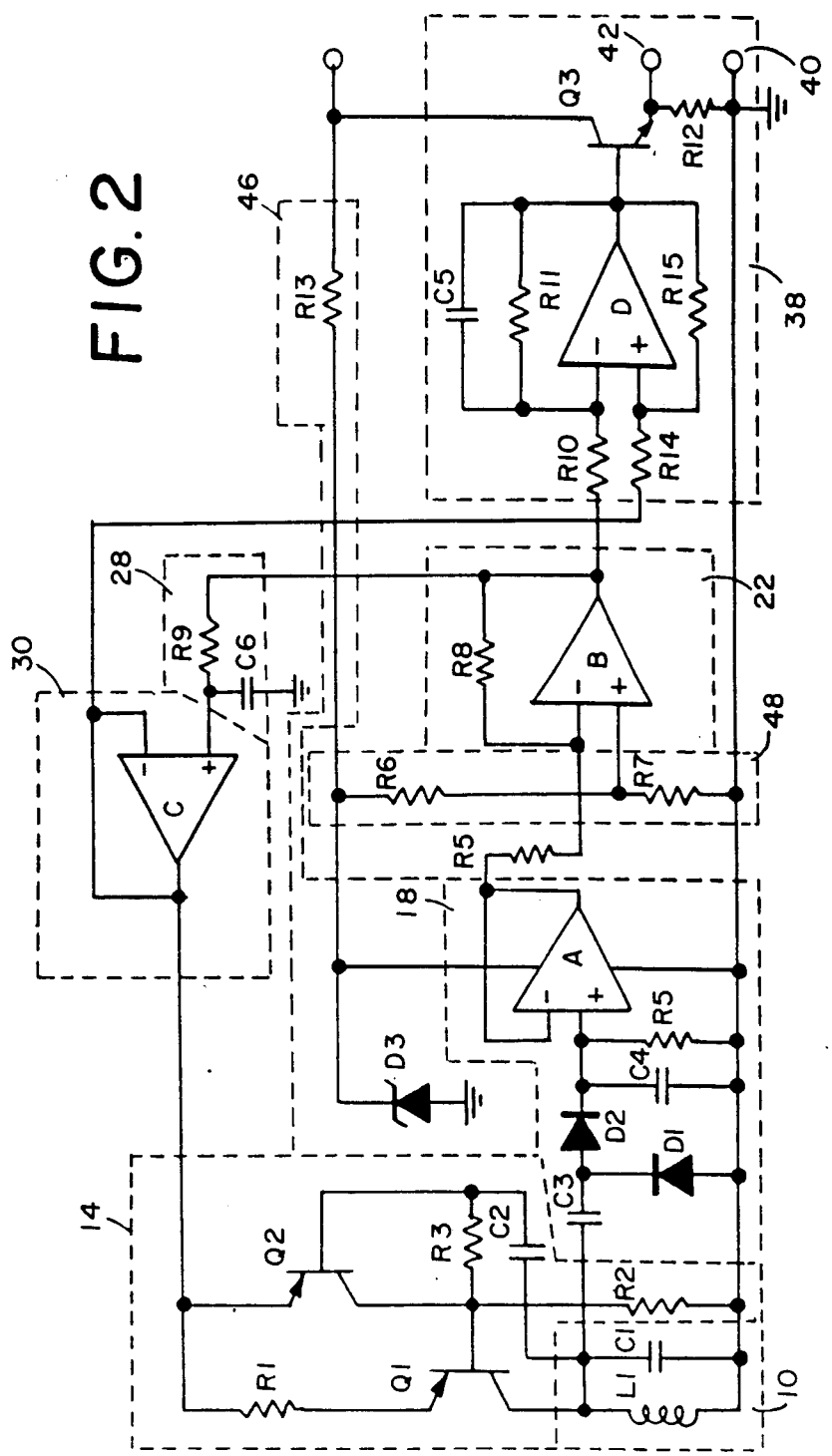
FIG. 2 is a detailed circuit diagram of the blocks shown in FIG. 1.

Turning to FIG. 2, the sensor 10 includes a sensing coil L1 connected in parallel with a capacitor C1. The oscillator 14 is a two transistor oscillator consisting of two inverting transistors Q1 and Q2 where the output of Q1 is connected 360° out of phase to the base of Q2. This regenerative feedback creates oscillation. The frequency of the oscillation is determined by the LC network of L1 and C1. An emitter resistor R1 limits the driving current to the tuned circuit supplied by supply circuit 30. Q2 is a self biased amplifier feeding transistor Q1 directly. L1 is exposed to the outside world and acts as a metal target sensing element of the detector. The base of Q2 is controlled by a resistor R3 and a capacitor C2. The output of the oscillator 14 is connected to the demodulator 18 which includes an input capacitor C3 and a simple diode doubler of D1 and D2.

The output of the diode doubler is processed by a capacitor C4 and a resistor R4 connected across the non-inverting input of an impedance matching operational amplifier A with unity gain which acts as a buffer for the diode doubler. A discharge resistor form the non-inverting input is used to maintain a bias voltage. The output signal of amplifier A is connected through a feedback loop to the inverting input of amplifier B. Amplifier B includes a non-inverting input which is set at a reference voltage above ground determined by the values of two series voltage dividing resistors R6 and R7. This establishes the output level of the oscillator 14. The amplification of this amplifier B is determined by the ratio of the negative feedback resistor R8 and the series input resistor R5. The level of amplifier gain influences the detector sensitivity. The higher gains create greater susceptibility to noise. Optimization is determined by the overall performance criteria necessary in the sensing application.

The filter 28 comprises a series RC network of R9 and C6 connected to the output of amplifier B with C6 referenced to ground. The DC voltage developed across the integrating capacitor C6 is immune to the intelligence signal above a specified or predetermined frequency from the output of amplifier B, thereby providing a true correcting voltage for the resultant oscillator tank Circuit Q losses. Since the filter 28 has a high output impedance, unity gain operational amplifier C transforms the impedance from high to low providing a stiff supply voltage 32 for the oscillator 14. This DC output voltage from Amplifier C is the supply voltage circuit 30 that supplies corrected operating voltage for the two transistor oscillator 14.

The output of amplifier B is also connected to an inverting input of amplifier D through a series resistor R10. Amplifier D includes an AC negative feedback through a resistor R11 and C5 connected in parallel from the output of amplifier D to its inverting input. The non-inverting input is connected to the output of amplifier C to provide the DC negative feedback. The AC feedback reduces the RF carrier frequency signal developed by the oscillator. This stage of the detector circuit provides additional amplification of the intelligence signal.

The output signal from amplifier D is connected to the base of a transistor Q3 which provides isolation between the output of amplifier D and the output terminal 42. The collector of Q3 is tied to the positive side of the supply voltage V+ while its emitter is connected to output resistor R12 between the output terminal 42 and ground 44.

Voltage regulation for the detector circuit is provided by a series resistor R13 and zener diode D3. This supplies the DC voltage $V_{reg.}$ for the various circuits of the detector.

Referring back to the metal target sensing element of the detector, L1 is an inductor providing the sensing. The tuned circuit L1-C1 of the two transistor oscillator 14 is comprised of a doughnut shaped coil that is physically located inside a ferrite cup core. This ferrite coil configuration is an open magnetic circuit, therefore, exposing its flux in a pattern that is effected by the presence of metal that is in close proximity to the open side of the cup core. The inductance is such that the resultant LC values provide the desired operating frequency. The Q of the tuned circuit is not critical, however, optimum performance is provided when the Q is greater than approximately twenty for most applications.

The RF voltage developed across the tuned circuit of the oscillator when undisturbed by metal moving across its path results in a constant level DC voltage at the output of amplifiers A,B,C and D. However, as metal is moved past the sensor 10 at a given rate, the RF signal level develops a modulated envelope whose resultant waveform 50 is demodulated and transformed into a varying level which is representative of the metal objects passing the sensor 10. This signal is amplified to levels where its electrical representation is well defined and easily utilized for intelligence information.

Thus the detector of the present invention with its supply voltage feedback loop to its oscillator circuit provides a constant amplitude intelligence signal over its sensing range. Moreover, unlike other detectors of this type, the correction voltage in addition provides temperature compensation which can effect the operation of known prior art detectors. Without the inclusion of a magnetic sensor, the detector of the present invention is able to sense both magnetic and non-magnetic metal targets passing by its sensing coil.

In summary, the detector of the present invention provides greater sensitivity, self-seeking threshold adjustment, temperature stability, reduced supply voltage variations on output performance, long term sensor stability as components of the detector circuit age, reliable sensing around and through stationary metallic objects that are in and around the sensing field, greater latitude in coil design of sensor and component values used in the circuit design, use of higher and lower Q's, simple and easy separation of electronics and coil by shielded cable, ease in setting upper and lower sensing frequency limits for all types of applications, elimination of magnetic drag found in mag-pickup devices for flow meter applications, a constant voltage intelligence output signal over both sensing frequency and distance range from sensor, low output impedance, sensing of all types of metals, reliable sensing under severe run-out conditions, greater sensing of smaller target mass and finally a reliable signal indications when the sensor is damaged by some foreign object or otherwise causing an open or shorted coil circuit by changing output signal status.

Although an embodiment of the invention has been illustrated in the accompanying drawings and described in the foregoing detailed description, it will be understood that the invention is not limited to the embodi-

I claim:

1. In an electronic metal detector for sensing both magnetic and non-magnetic metals in motion having an oscillator including a sensing coil whose Q varies when metal targets are brought within the magnetic field generated by said coil, said Q variations creating a change in the amplitude of the oscillations produced by the oscillator, the improvement comprising:
   an intelligence circuit means connected to said oscillator for generating a usable intelligence signal comprised of a DC voltage level and an AC voltage component representative of the movement of metal targets past said coil; and
   means connected to said intelligence circuit means and receiving said intelligence signal for generating a feedback DC supply voltage without the AC voltage component of the intelligence signal to operate said oscillator in a manner to maintain a predetermined and constant amplitude of oscillation throughout the sensing range of the coil whether the metal targets are stationary or moving at various speeds.

2. An improved detector of claim 1, further including a low pass filter connected between the oscillator and intelligence circuit electrically having a time constant to filter out the intelligence portion of said signal representative of the metal targets but permitting the feedback of said signal representing the sensing of stationary and slow moving metals to correct for Q losses in the oscillator.

3. An improved detector of claim 1, further including a means for amplifying the intelligence signal having two inputs and and output, said amplifying means having one input connected to the supply voltage of the oscillator and the other input connected to the intelligence signal so that the portions of the signal representing the stationary and slow moving metals is canceled out of the intelligence signal leaving only the intelligence for amplication and generation at the output of said amplifying means.

4. An improved detector of claim 1, further including a reference voltage means and a second amplifying means having two inputs and an output, said reference voltage means is connected to one input of said second amplifying means and the other input is connected to the intelligence signal so that the RF output of the oscillator is set at a predetermined threshold level of sensing.

5. An improved detector of claim 1, wherein the intelligence circuit means includes a demodulator means having a diode double connected to the output of said oscillator for converting the modulated RF output signals from the oscillator into a DC signal having an AC component thereon.

6. An electronic metal detector for sensing magnetic and non-magnetic metals in motion, comprising:
   an oscillator having a sensing coil effected by the presence of both stationary and moving metals within its field of sensing and an output for generating modulated RF signals having signatures according to the motion of the sensed metals;
   a demodulator connected to the output of the oscillator for receiving said RF signals and conditioning the same to produce output signals proportional to the RF signals having a composite waveform of a DC level with an AC component representative of the signatures of the sensed metals;
   means connected to said demodulator and receiving its output signals for generating intelligence signals with the AC component representative of the motion of the metals past the sensing coil and for generating a DC feedback supply voltage for operating said oscillator, said means having a feedback path connected to the oscillator for connecting the supply voltage to the oscillator to maintain a predetermined and constant amplitude of oscillation throughout the sensing range of the coil, said means further including a low pass filter for blocking the intelligence portion of the signal in the supply voltage feedback path and including means for eliminating the signals representing stationary and slower moving metals from the intelligence signals output from said generating means.

7. A detector of claim 6 wherein said oscillator includes two transistors connected in an inverted configuration in which the output of one is connected 360° out of phase to the base of the other to create a regenerative feedback oscillations.

8. A detector of claim 7 wherein the emitter circuits of each transistor are connected to the DC feedback supply voltage of said generating means to provide the operating voltage for said oscillator and for correcting for the Q losses of the sensing coil by stationary and slower moving metals while maintaining a constant amplitude of oscillations during the sensing of the desired metal targets.

9. A detector of claim 8 wherein the electronic circuitry of the detector is mounted within a probe capable of being mounted within a stainless steel housing of a flow meter whereby the DC feedback supply voltage compensates for the Q losses due to the stainless steel housing while permitting the sensing coil to see through the stainless steel and detect a moving metal target on the other side thereof.

10. A detector of claim 6 further including circuit means connected to the feedback path at one end and to an input of the intelligence signals means for acting in conjunction with said feedback supply voltage path to said oscillator so that the combination of the circuit means and feedback path compensates and provides greater sensitivity, temperature stability, compensation for component variations in circuitry, lower and higher usable Q values in the oscillator, elimination of magnetic drag in sensing metals, a constant intelligence signal output over sensing frequency and sensing distance of the coil, reliable sensing during run-out conditions and the ability of sensing the desired metal target within a field of stationary metals and metal moving below a predetermined rate of speed past the sensing coil of the detector.

11. A detector of claim 6 wherein said generating means includes an intelligence signal differential amplifier means for sensing both an open or shorted sensing coil circuit and for generating a reliable signal indication of such condition of the coil.

12. An electronic proximity detector usable in flow meter applications for sensing magnetic and non-magnetic vanes rotating in the housing of the flow meter to determine the rate of fluid flow therethrough, comprising:
   an oscillator for generating modulated signals representative of the motion of the vanes and having a coil sensing each vane as it passes within its field of sensing to produce said modulated signals:

a demodulator circuit connected to the output of the oscillator for receiving the modulated signals and generating a demodulated output signal representative of the speed of said vanes;

an inverting amplifier connected to the output of the demodulator circuit and receiving the demodulated signals to provide an intelligence signal representative of the motion of the vanes past the coil, said amplifier having two outputs;

an intelligence signal amplifier circuit having a low pass filter connected to one of the inverting amplifier outputs for blocking the intelligence portion of the signal for generating a correction signal DC feedback acting as the supply voltage for the oscillator to maintain a predetermined and constant level of oscillation amplitude for the oscillator over its sensor coil range while correcting for Q losses due to stationary or slow moving metals within the field of the sensor coil; and means for amplifying the intelligence signal connected to the other output of the inverting amplifier having an input connected to the correction signal DC feedback for generating a usuable intelligence signal output proportional to the number of vanes sensed without the modulated signals representing the stationary and slow moving metals interfering with the usable signal.

* * * * *